(12) United States Patent
Lucey et al.

(10) Patent No.: US 11,154,447 B2
(45) Date of Patent: Oct. 26, 2021

(54) ORTHOPEDIC DEVICE AND METHOD FOR LOWER LIMB ELEVATION AND STABILIZATION

(71) Applicant: BONE FOAM, INC., Corcoran, MN (US)

(72) Inventors: Stephen Davis Lucey, Greensboro, NC (US); Chad L. Robran, Plymouth, MN (US)

(73) Assignee: BONE FOAM, INC., Corcoran, MN (US)

( * ) Notice: Subject to any disclaimer, the term of this patent is extended or adjusted under 35 U.S.C. 154(b) by 24 days.

(21) Appl. No.: 16/668,617

(22) Filed: Oct. 30, 2019

(65) Prior Publication Data

US 2020/0060917 A1    Feb. 27, 2020

Related U.S. Application Data

(63) Continuation-in-part of application No. 15/676,643, filed on Aug. 14, 2017, which is a
(Continued)

(51) Int. Cl.
*A61G 7/05* (2006.01)
*A61G 13/12* (2006.01)
(Continued)

(52) U.S. Cl.
CPC .............. *A61G 13/125* (2013.01); *A61F 5/37* (2013.01); *A61F 5/3769* (2013.01);
(Continued)

(58) Field of Classification Search
CPC .......... A61G 13/00; A61G 13/12; A61G 7/07; A61G 7/075; A61G 7/0755; A61F 5/00; A61F 5/01; A61F 5/0111; A61F 13/00
See application file for complete search history.

(56) References Cited

U.S. PATENT DOCUMENTS

| 2,478,492 A | 8/1949 | Morrison |
| 2,478,497 A | 8/1949 | Morrison |

(Continued)

OTHER PUBLICATIONS

U.S. Appl. No. 15/676,643, filed Aug. 14, 2017, Office Action dated Apr. 5, 2018.
(Continued)

*Primary Examiner* — Peter M. Cuomo
*Assistant Examiner* — Ifeolu A Adeboyejo
(74) *Attorney, Agent, or Firm* — Workman Nydegger

(57) ABSTRACT

A support device provides elevation and support for a patient's foot, including ankle and heal, and limits lateral and medial rotation of the foot. This protects the knee from injury while healing. The device includes a generally flat main body, two spaced-apart lateral ridges, and a medial depression between the lateral ridges that provides a support surface on which the foot may be positioned. The lateral ridges can extend to a height above the support surface so that inner side surfaces of the lateral ridges are adjacent to a majority of a foot placed in the medial depression. The lateral ridges can terminate below a top of the foot to permit unrestricted ventilation and access to the foot. The lateral ridges can be spaced apart to facilitate placement of a foot onto and removal of the foot from the support surface without manual manipulation of the device.

20 Claims, 4 Drawing Sheets

Related U.S. Application Data continuation-in-part of application No. 14/709,630, filed on May 12, 2015, now abandoned.

(51) Int. Cl.
| | | |
|---|---|---|
| *A61G 13/10* | (2006.01) | |
| *A61G 7/057* | (2006.01) | |
| *A61F 5/37* | (2006.01) | |
| *A61G 7/075* | (2006.01) | |

(52) U.S. Cl.
CPC ....... *A61G 7/05723* (2013.01); *A61G 7/0755* (2013.01); *A61G 13/10* (2013.01); *A61G 2200/56* (2013.01); *A61G 2210/50* (2013.01)

(56) References Cited

U.S. PATENT DOCUMENTS

| | | | |
|---|---|---|---|
| 2,911,657 A | 11/1959 | Streter, III | |
| 3,511,233 A | 5/1970 | Holy | |
| 3,639,927 A | 2/1972 | Munch | |
| 3,742,528 A | 7/1973 | Munch | |
| 3,901,228 A | 8/1975 | Brown | |
| 3,903,878 A | 9/1975 | Spann | |
| 3,931,654 A | 1/1976 | Spann | |
| 3,946,451 A | 3/1976 | Spann | |
| 4,071,031 A | 1/1978 | Lowman | |
| 4,104,746 A | 8/1978 | Goetz | |
| 4,135,504 A | 1/1979 | Spann | |
| 4,186,738 A | 2/1980 | Schleicher | |
| 4,364,135 A | 12/1982 | Emmerich nee Giesche | |
| 4,782,827 A | 11/1988 | Paratte | |
| RE22,090 E | 10/1989 | Berguer | |
| RE33,090 E | 10/1989 | Berguer | |
| 5,046,487 A | 9/1991 | Scott | |
| 5,149,033 A | 9/1992 | Burzler | |
| D359,190 S | 6/1995 | Hargest | |
| 5,477,866 A | 12/1995 | Davenport | |
| 5,584,303 A | 12/1996 | Walle | |
| 5,603,336 A | 2/1997 | Shepich | |
| 5,603,692 A | 2/1997 | Maxwell | |
| 5,716,334 A | 2/1998 | Wade | |
| 5,725,486 A | 3/1998 | Engelman | |
| 5,745,939 A | 5/1998 | Flick et al. | |
| 5,957,874 A | 9/1999 | Klein | |
| 5,997,491 A | 12/1999 | Harris | |
| 6,000,401 A | 12/1999 | Herrick | |
| 6,468,239 B1 | 10/2002 | Mollura | |
| 6,572,573 B1 | 6/2003 | Klein | |
| 6,622,727 B2 | 9/2003 | Perry | |
| 6,935,697 B2 | 8/2005 | Conlon | |
| 7,228,580 B2 | 6/2007 | Dalton | |
| 8,479,333 B2 | 7/2013 | Gould | |
| 8,491,513 B2 | 7/2013 | Flam | |
| 8,771,213 B2 | 7/2014 | Wens | |
| D718,456 S | 11/2014 | McNamee | |
| D748,931 S | 2/2016 | Corigilano | |
| 9,829,147 B2 | 11/2017 | Baker | |
| 2014/0101854 A1 | 4/2014 | Watson | |
| 2015/0027451 A1* | 1/2015 | McNamee | A61F 5/3761 128/882 |
| 2016/0331574 A1 | 11/2016 | Lucey et al. | |
| 2018/0008499 A1 | 1/2018 | Lucey et al. | |

OTHER PUBLICATIONS

U.S. Appl. No. 15/676,643, filed Aug. 14, 2017, Final Office Action dated Nov. 2, 2018.
U.S. Appl. No. 15/676,643, filed Aug. 14, 2017, Office Action dated May 23, 2019.
U.S. Appl. No. 15/676,643, filed Aug. 14, 2017, Final Office Action dated Aug. 9, 2019.
U.S. Appl. No. 14/709,630, filed May 12, 2015, Office Action dated Aug. 11, 2016.
U.S. Appl. No. 14/709,630, filed May 12, 2015, Final Office Action dated May 26, 2017.

* cited by examiner

ORTHOPEDIC DEVICE AND METHOD FOR LOWER LIMB ELEVATION AND STABILIZATION

CROSS REFERENCE TO RELATED APPLICATION

This Application is a continuation-in-part of U.S. patent application Ser. No. 15/676,643, filed Aug. 14, 2017, which is a continuation-in-part of U.S. patent application Ser. No. 14/709,630, filed May 12, 2015, abandoned, the disclosures of which are incorporated herein by reference in their entirety.

BACKGROUND

Following injury or a lower limb surgical procedure, especially knee surgery (such as total knee replacement, arthroscopic knee surgery, or ACL surgery), a patient often lies or is placed in a supine position, i.e. with the front (anterior) portion of the lower limb facing up and the back portion of the lower limb (posterior) facing downward. As part of the recovery, it is often required that the lower limb remain in a certain position, being isolated, immobilized, and elevated, for a prescribed time period.

Many kinds of undesirable movements are possible, however, during this time period of recovery. For example, natural movement may arise as the patient's foot naturally tends to rotate outwardly (laterally) or inwardly (medially) from the supine position. This lateral or medial foot rotation can exert undesirable torsion on an injured or newly repaired knee, potentially slowing recovery and possibly necessitating more surgery to fix any damage. Other undesirable movements may also need restraint.

In the context of medical recovery of extremity trauma, efforts may be taken to ensure that a patient's body is properly elevated, isolated, stabilized, and/or otherwise supported. The patient may lie, for example, in a supine position, with the ankle required to be isolated, elevated, immobilized, and supported. Furthermore, the natural inclination of the foot to rotate outwardly (laterally) or inwardly (medially) due to relaxation or gravity may in turn cause the tibia and fibula to rotate laterally or medially relative to the femur. This in turn may cause unwanted and potentially dangerous torsion or torque to the knee joint. For example, a patient recovering from knee surgery may incur serious pain, reinjure the knee, and even require additional surgery if the knee is not properly protected from torsion.

For example, U.S. Pat. No. 8,491,513 to Flam et al. illustrates several prostheses that are designed to cushion a patient's foot and prevent pressure points from causing pain when a patient is bedridden for lengthy periods of time. However, none of the prostheses are configured or described as being able to prevent free rotation of the patient's foot. The prosthetic devices are either too shallow (e.g., FIGS. 6B, 13A showing a prosthesis body 20B with a maximum sidewall height of 2 inches at the heal and a sidewall height of only 1.5 inch for the rest of the foot) to provide any meaningful limit to foot rotation and/or they are curved (e.g., FIG. 6C, showing a prosthesis body 20C having a curved bottom surface) to facilitate rotation of the foot in case the patient wishes to turn on their side and/or they are merely a foot sleeve (e.g., FIGS. 2A, 3A, 4) having a bottom surface that is too narrow to prevent foot rotation. FIG. 13A shows a mannequin leg and foot placed in the shallow cavity of the prosthesis of FIG. 6B, which is configured to underlie, contact, and support the patient's leg and calf muscle, which can be problematic in cases where it is desired to raise the foot high enough to lift the calf muscle and lower leg below the knee off the bed to maintain the knee in a straightened or extended position.

U.S. Pat. No. 3,901,228 to Brown discloses a therapeutic foot rest that suffers from tightly placed sidewalls that are designed to totally encase the foot and which must be manually spread apart when inserting or removing the patient's foot from the device. This prevents a patient's foot from being placed vertically downward into or being lifted vertically upward from a foot supporting depression inside the device without outside assistance in the case of an incapacitated patient, or requiring the patient to sit up and spread the sidewalls apart themselves when installing or removing the foot rest. In either case, the inherent difficultly of having to spread apart the tightly positioned wall using both hands to insert or remove the foot may cause discomfort or, if the foot is accidentally torqued or dropped, unintentional injury to the knee. Because the Brown device is configured to completely encase the foot, it limits essentially all foot movements, including plantarflexion, rotation dorsiflexion, etc., prevents adequate ventilation of the foot, and impedes ready access to the foot (e.g., to provide triage). In the case where outside assistance is unavailable, or the foot is otherwise not removed from the encasement within a prescribe period of time, the totally encased foot can become overheated, infected, possibly suffer permanent damage, and possibly cause sickness, or even amputation of the extremity.

U.S. Pat. No. 8,771,213 to Wens that is configured to hold and restrain both feet and legs of an incapacitated patient, such as a patient with paralysis. This prevents independent movement of either or both legs, which can be unduly constraining when a patient only wishes to hold and restrain the foot of the affected leg while permitting free and independent movement of the other leg. Similar to devices in Flam et al., the Wens device is designed to support both the feet and lower legs, including the calves, of the patient. This prevents the calves and lower legs from being suspended above the bed or other surface supporting the patient's body. Extended contact between a patient's calves and lower legs and the support surface can restrict blood circulation, causing deep vein thrombosis, and result in bed sores.

BRIEF SUMMARY

Disclosed herein are orthopedic devices configured for supporting and restraining rotation of the foot of a patient who is recovering from surgery, such as knee surgery. The devices help maintain knee extension and unwanted torsion on the knee joint by restraining foot rotation. Continuous extension and of a surgically repaired knee and protection against unwanted torsion of the knee following surgery promote proper healing.

In some embodiments, devices disclosed herein can be configured to elevate the foot and ankle to a level that lifts the knee above the surface on which the patient lies (e.g., floor, table, bed, couch, or other surface) so that the posterior side of the knee remains unsupported. This allows gravity to pull down on the posterior side of the knee, stretching and maintaining proper extension of the knee. Also, elevating the ankle and lower leg above the surface may be desirable to ensure proper blood flow for reduction of edema and promotion of healing.

Devices disclosed herein are configured to limit unwanted motion of the foot to stabilize and protect the recovering knee. For example, when the patient is lying in a supine position, the foot tends to rotate outwardly (laterally) or inwardly (medially) due to relaxation or gravity, which may, in turn, cause the tibia and fibula to rotate laterally or medially relative to the femur. This rotation may cause unwanted and potentially dangerous torsion or torque to a recovering knee joint. For example, a patient recovering from knee surgery may incur serious pain, reinjure the knee, and/or even require additional surgery if the knee is not properly protected from such torsion. The disclosed devices are configured to cradle and support the foot, including the ankle and heel, in a manner that prevents such rotations and allows the knee to be free of torsional moments.

Support devices as disclosed herein may be used to isolate, elevate, immobilize, and support an ankle to provide restraint against foot and lower leg rotation. The patient may lie, for example, in a supine position, with the foot, including ankle and heel, resting on or in a cavity of continuous or varying depth formed in the support device. The support device may include a main body with a generally flat lower surface, which can be sufficiently wide to prevent or limit unwanted rotation of the support device in response to foot rotations. The support device includes two spaced-apart lateral ridges extending upwardly along or near lateral edges of the main body, and a medial depression between the lateral ridges that provides a support surface and cavity of continuous or varying depth on and in which the foot and ankle may be positioned. The lateral ridges can be sufficiently tall relative to the foot to restrain the foot from medial and lateral rotations. The lateral ridges can be spaced apart to permit a foot to be placed into or lifted out of the medial depression without having to manipulate the support device (e.g., without having to spread the lateral ridges apart when inserting a foot into or removing the foot from the medial cavity). This ease of insertion and removal helps prevent injury to the patient's knee.

The support device may further comprise a medial ridge connected to and extending transversely between the lateral ridges to limit plantar flexion of the foot during recovery. The support device can terminate at a location proximal to the ankle and distal to the calf muscle so that the calf muscle and region behind the knee are not in contact with the support device and, in some embodiments, are not in contact with surface on which the patient lies. This assists in maintaining the knee in an extended position.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Disclosed herein are orthopedic devices configured for supporting and restraining rotation of the foot of a patient who is recovering from surgery, such as knee surgery. The devices help maintain knee extension and unwanted torsion on the knee joint by restraining foot rotation. Continuous extension and of a surgically repaired knee and protection against unwanted torsion of the knee following surgery promote proper healing. Some embodiments are designed to also limit plantar flexion of the foot.

For lower limb medical recovery, such as following knee surgery or injury, a patient often lies or is placed in a supine position, i.e. with the front (anterior) portion of the lower limb facing up and the back portion of the lower limb (posterior) facing down. As part of the recovery, it is often required for the lower limb to remain in a certain or fixed position, being isolated and elevated, for a period of time. Also, elevating the lower leg from the bed surface may be desirable to ensure proper blood flow for reduction of edema and promotion of healing. Other benefits from elevating the leg may be realized. Rotation of the foot may cause detrimental rotation of the lower leg. The twisting or torsioning effect on the leg may slow the process of healing, cause pain, and even cause further injury to the knee joint following knee injury or surgery. Thus, support devices are needed to elevate lower limbs and immobilize the foot and ankle to ensure proper positioning and proper healing.

Figure 1:
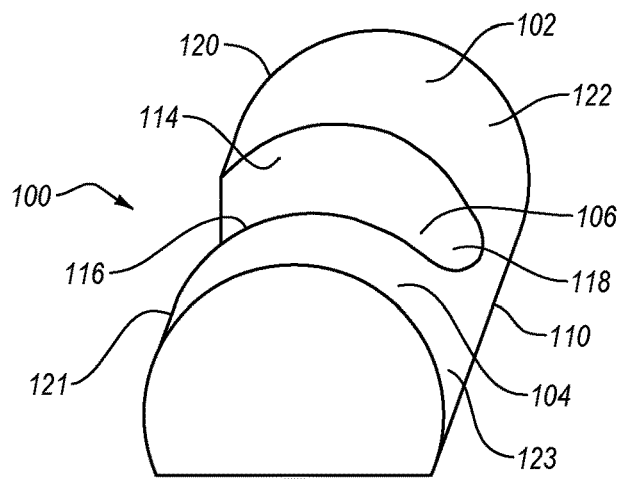
FIG. 1 is a perspective view of a device having two lateral ridges and a medial depression between the ridges for lower limb elevation and foot immobilization, including restraint of foot rotation.

FIG. 1 is a perspective view illustrating an embodiment of a support device 100 for lower limb (e.g., foot, ankle, and knee) elevation and stabilization. The support device 100 comprises a main body 110 having a generally flat bottom surface, two spaced-apart lateral ridges 102, 104 extending upwardly away from main body 110 along or near lateral edges of main body 110, and a medial depression 106 between lateral ridges 102, 104 that provides a support surface 118 on which a foot, including ankle 113 and heel 112 (FIG. 3B), of a patient may be positioned. As shown, support device 100 has a single medial depression that comfortably receives and supports a single foot while permitting independent movement of the patient's other foot and leg.

Lateral ridges 102, 104 may include inner side surfaces 114, 116 extending upward from support surface 118 and that can contact the foot, when placed on support surface 118 within medial depression 106 and restrain medial and/or lateral rotation of the patient's foot. Lateral ridges 102, 104 further include distal upper surfaces 120, 121 and proximal upper surfaces 122, 123 on left and right sides of main body 110, respectively.

From main body 110 with generally flat bottom surface, lateral ridges 102, 104 extend generally vertically upward and are located near or at along sides of main body 110. Lateral ridges 102 and 104 may span a desired distance along the width of main body 110, or span an entire side of main body 110. In some embodiments, lateral ridges 102, 104 have lengths that extend beyond one or more main body edges, creating an overhang wall formation.

Lateral ridges 102, 104 can be integrally formed or interlocked with main body 110 in a manner that ensures they remain in an upright position during use to restrain lateral or medial rotation of the foot. Lateral ridges 102, 104 can extend beyond (e.g., above) support surface 118 to a height so that a significant portion (e.g., ⅓, ½, or ⅔) of the foot is adjacent to side surfaces 114, 116 during use (as illustrated in FIG. 3B). In some embodiments, lateral ridges 102, 104 can extend beyond at least the heel supporting region of support surface 118 by at least 3 inches, at least 3.5 inches, at least 4 inches, at least 4.5 inches, at least 5 inches, at least 5.5 inches, or at least 6 inches.

When the foot exerts rotational forces to inner side surfaces 114, 116, such forces can be transferred by lateral ridges 102, 104 to the bottom surface of main body 110, which transfers forces to a surface upon which main body 110 is placed. The bottom surface of main body 110 is advantageously sufficiently wide ensure that main body 110 does not rotate in response to rotational forces from the foot. In some embodiments, the bottom surface of main body 110 can have a width from left to right of at least 6 inches, at least 7 inches, at least 8 inches, at least 9 inches, at least 10 inches, at least 11 inches, or at least 12 inches.

Figure 2:
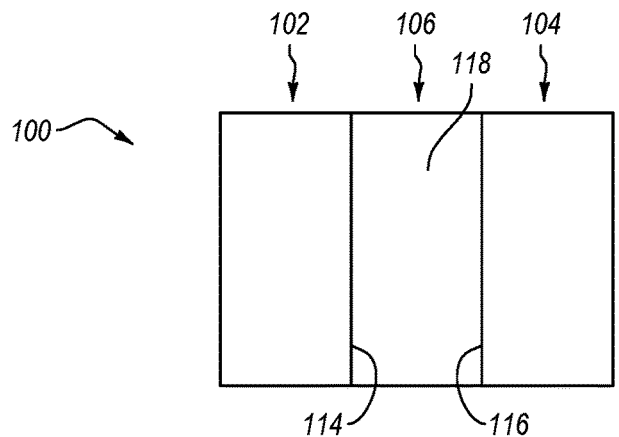
FIG. 2 is a top view of the device of FIG. 1 for lower limb elevation and foot immobilization, including restraint of foot rotation.

FIG. 2 is a top schematic view of support device 100, with main body 110, lateral ridges 102, 104, medial depression 106, support surface 118, and inner side surfaces 114, 116 seen from above. As illustrated, main body 110 may include a generally rectangular body. Alternatively, the shape of main body 110 may be multi-sided with sharp or rounded corners, such as rectangular, trapezoidal, or rectilinear, oblong, oval, circular, or have other shapes, proportions, and dimensions. The length may be larger than the width or, alternatively, the width may be larger than the length. Edges may be defined with sharp edges, curved edges, or a combination thereof.

The width, or wall thickness, of lateral ridges 102, 104 may be the same or they may vary. In some embodiments, at least one of lateral ridges 102, 104 can have a thickness of at least 0.75 inch, at least 1 inch, at least 1.25 inch, at least 1.5 inch, at least 1.75 inch, at least 2 inches, at least 2.25 inches, at least 2.5 inches, at least 2.75 inches, or at least 3 inches. Although the widths of lateral ridges 102, 104 are shown as being homogeneous in spanning main body 110 in a parallel manner, the widths may have varying dimensions such that one or more of inner side surfaces 102, 104 extends in a path that is not truly crosswise. For example, the width between inner side surfaces 114, 116 may be narrowed or tapered inwardly near or at a region where the ankle 113 and heel 112 would be located on support surface 118 (FIG. 3B). Alternatively, the width between inner side surfaces 114, 116 may be tapered outward from a center region where the ankle 113 and heel 112 would be located on support surface 118.

Support surface 118 in medial depression 106 may be contoured to conform to, e.g., contact and support, one or more of the lower leg distal to the calf, heel, ankle region, and talus bone of the patient. To conform to the lower leg, heel, ankle region, and talus bone of the patient, inner side surfaces 114, 116 may have notches, or hollowed out cavities, removed near or at the center area where the ankle and heel are located on support surface 118 when placed in depression 106. Alternatively, or additionally, a vertical hollowed out indention in each inner side surface 114, 116 of lateral ridges 102, 104 may be provided, forming a vertical hollow on each inner side surface 114, 116 to accommodate the talus bone. Providing a hollowed section, whether it be a cavity or vertical hollow, on each inner side surface 114 and 116 allows the support device 100 to be used for either a left foot or right foot.

Support surface 118 of medial depression 106 may be generally flat; however, embodiments include a variety of different surfaces, including a surface that is curved, rounded, wavy, concave, convex, slanted upward, curved upward, slanted downward, curved downward, as well as a variety of other surfaces. In some embodiments, support surface 118 is curved and slanted upward or downward, providing a curving slope that better conforms to the heel and ankle when the foot is placed in depression 106. In some embodiments, there may be a second depression within depression 106 providing an elevationally lower region of support surface 118. For example, support surface 118 may include a lower cutout portion to accommodate the heel, which is typically elevationally lower than the rest of the foot and ankle when the foot is in a supine position. This permits a heel of a foot to be sunken into the second depression (or cutout portion) below the level of depression 106, thereby providing a support surface 118 with a first upper level supporting the ankle and a second lower level supporting the heel. This may help to further isolate the heel from movement and thereby further restrain leg, foot, and ankle rotation (medial and/or lateral), as well as allowing the support surface 118 in the depression 106 to comfortably support the natural contours of the ankle and heel.

In some embodiments, at least a portion of a distal upper surface of one of the spaced-apart lateral ridges 102, 104 can have a downward slope declining towards a proximal end. As shown, both distal upper surfaces 120, 121 have downward slopes. In other embodiments, only one distal upper surface may have a downward slope.

In some embodiments, at least a portion of a proximal upper surface of one of the spaced-apart lateral ridges 102, 104 can have a downward slope declining towards a proximal end. As shown, both proximal upper surfaces 122, 123 have downward slopes; however, in some embodiments, only one proximal upper surface may have a downward slope.

The downward slope may be a curved, or rounded, downward slope. The combined proximal upper surfaces 122, 123 and distal upper surfaces 120, 121 may form an upside down, cupping shape. Any suitable shape may be provided, however. For example, instead of a curved shape, the combined upper surfaces may be generally flat, creating a standard wall appearance.

Outer edges of the proximal upper surfaces 122, 123 and distal upper surfaces 120, may be sharp, blunt, or be rounded and smoothed out. For height, lateral ridges 102, 104 may have the same or similar height; however, their heights may differ. Also, there may be differences in curvatures and edges, shapes, length, and width. The height of lateral ridges 102, 104 and/or width between inner side surfaces 114, 116 can be selected to accommodate a foot of any size. For smaller feet, the height of lateral ridges 102, 104 and/or width between inner side surfaces 114, 116 can be reduced. For larger feet, the height of lateral ridges 102, 104 and/or width between inner side surfaces 114, 116 can be increased.

One or both of lateral ridges 102, 104 may extend generally vertically upward to a height of at least a significant portion (e.g., at least ⅓, at least ½, or at least ⅔) a general foot length according to anatomical measurements of a standard person. In this way, inner side surfaces 114, 116 of lateral ridges 102, 104 can abut the sides of a patient's foot 111 and thereby restrain medial and/or lateral rotation. A standard person is a mathematical model of a person based on any suitable data that simulates a person's size, body proportions, and the like. The model can be based upon data, for example, used in the clothing and shoe industry to define sizes for apparel and the like. The standard person used and the data set used to de the standard person is chosen with the user of support device 100 in mind and can be based upon average values of body proportions from any sample of the population from, for example, total population, gender, age, body size or weight, nationality, or the like. The standard person may also be based upon any particular individual, or group of individuals. Thus, the standard person for a particular support device 100 may be designed for marketing to the public in general, or be customized to fit a particular group of people, or to fit an individual.

Figure 3A:
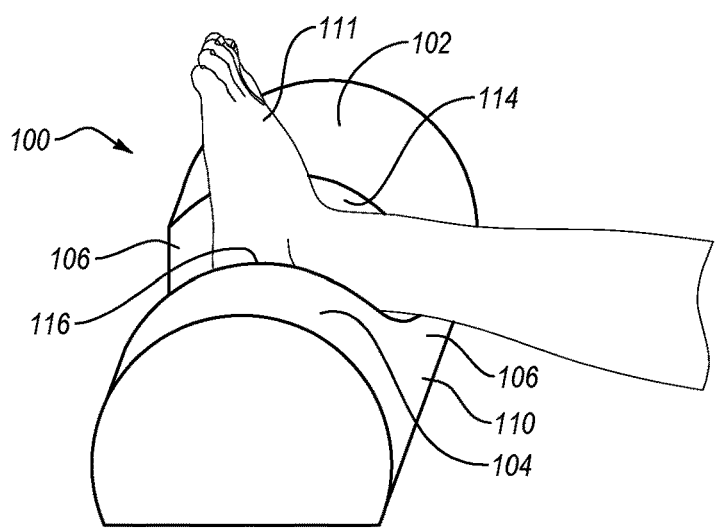
FIG. 3A is a perspective view of a foot inserted into the device of FIG. 1 for lower limb elevation and foot immobilization, including restraint of foot rotation.
Figure 3B:
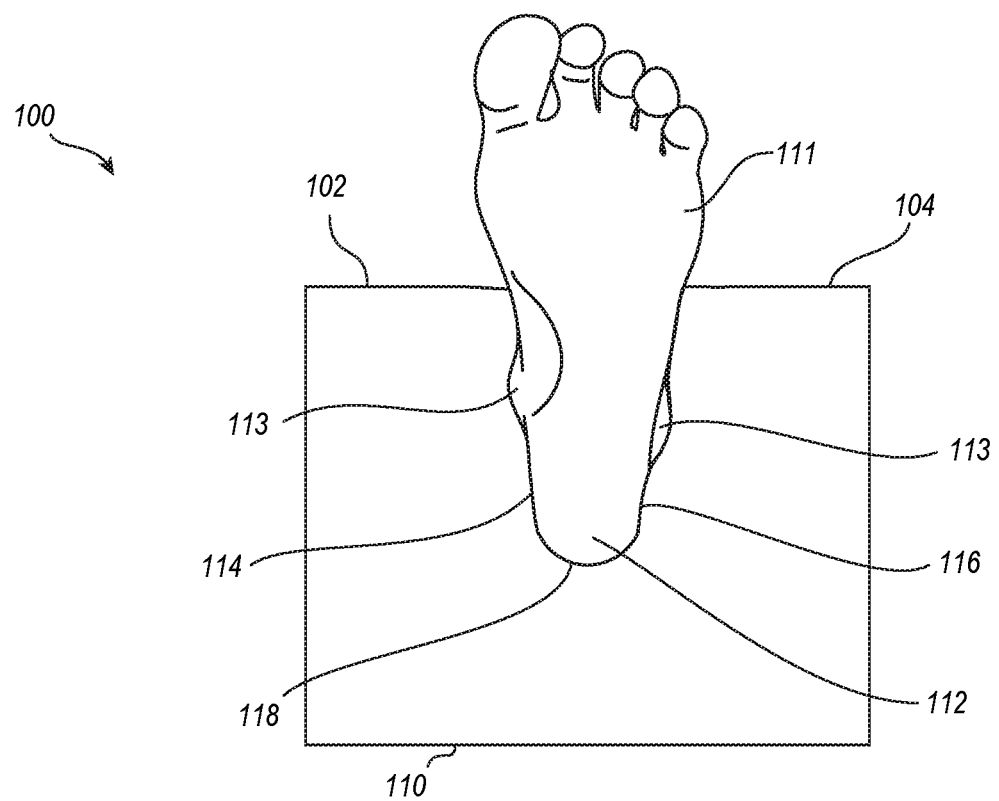
FIG. 3B is an end view of the device of FIG. 3A with a foot inserted into the device for lower limb elevation and foot immobilization, with lateral and medial sides of the foot being restrained from rotations by adjacent lateral ridges.
Figure 3C:
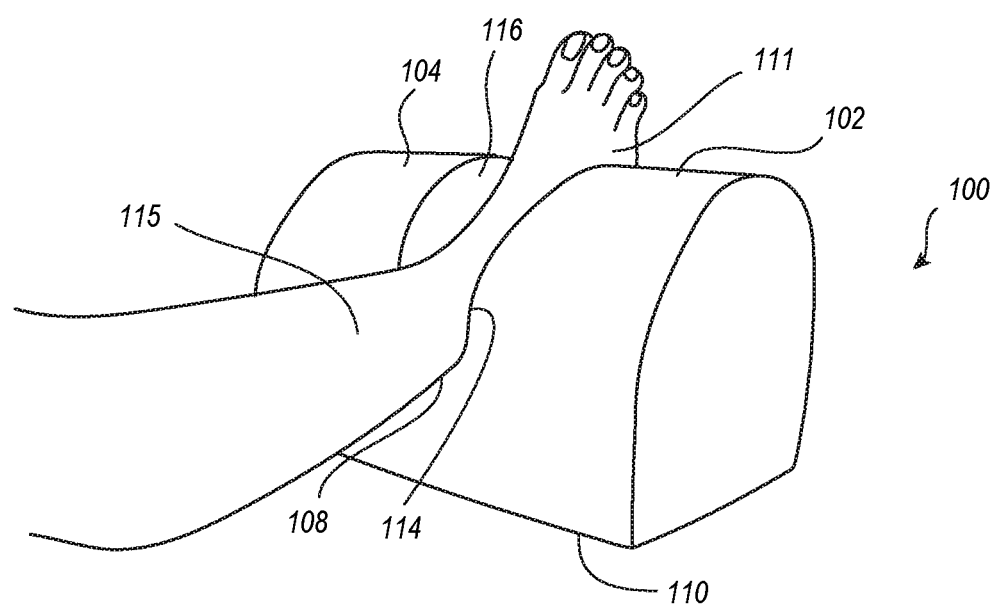
FIG. 3C is an alternative perspective view of the device of FIG. 3A with a foot inserted into a device for lower limb elevation and foot immobilization, including restraint of foot rotation.

Turning to FIGS. 3A-3C, a foot 111 is shown inserted into medial depression 106 of support device 100, with the ankle 113 and heel 112 of foot 111 resting on support surface 118 of medial depression 106 between inner side surfaces 114, 116 of lateral ridges 102, 104. The foot 111 may face generally upward with toes pointing upward, as shown. However, the foot 111 may be tilted or angled with a side of the foot 111 resting against one of inner side surfaces 114, 116. Lateral ridges 102, 104 may be spaced to provide a tight fit or a relaxed fit holding foot 111. Furthermore, medial depression 106 may be spaced with ample wiggle room to the extent that that an ankle need not fully touch inner side surfaces 114, 116. As further illustrated in FIGS. 3A-3B, lateral ridges 102, 104 and side surfaces 114, 116 of support device 100 can be spaced apart sufficiently to permit a foot to be placed downwardly into or lifted upwardly out of medial depression 106 without having to manually manipulate the support device (e.g., without having to manually spread apart lateral ridges 102, 104 when inserting a foot into or removing the foot from medial depression 106). This ease of insertion and removal helps prevent injury to the patient's knee. As also illustrated in FIGS. 3A and 3C, support device 100 is devoid of any walls that contact the top (or anterior surface) of a foot placed in medial depression 106 that could limit potentially desirable foot movements, such as dorsiflexion, toe flexion, circumduction, eversion, or inversion, and also limit ready access to the anterior foot region. In many cases, it is desirable to permit dorsiflexion, or both plantar flexion and dorsiflexion, in order to permit therapeutic range of motion and prevent or reduce numbness or stiffness of the foot during healing of the knee.

In some embodiments, support surface 118 and/or medial depression 106 may provide adjustments such that the space between may be increased or decreased, as needed. For example, the lateral ridges 102, 104 may be moved inward and outward along the main body 110 to form a smaller or larger space, respectively. Alternatively, inserts may be added and removed to either or both of inner side surfaces 114, 116 to change the space of medial depression 106. Appropriate attachments for adjustments may include screws, clamps, straps, and other means commonly known in the art. Lateral ridges can be spaced apart to permit a foot to be placed into or lifted out of the medial depression without having to manipulate the support device (e.g., without having to spread the lateral ridges apart when inserting a foot into or removing the foot from the medial cavity). This ease of insertion and removal helps prevent injury to the patient's knee.

Additional materials may be added to provide further support, compression, structure, and weight. For example, cushioning may be added along inner side surfaces 114, 116 of lateral ridges 102, 104 to provide a snug or tight fit when a foot 111 is inserted within medial depression 106. Cushioning may be added in select areas along inner side surfaces 114, 116 of the lateral ridges 102, 104 that abut sides of the patient's foot, for example, near or at the location where the ankle and heel are to be placed. Alternatively, cushioning may be added on only one side, either inner side surface 114 of lateral ridge 102 or inner side surface 116 of lateral ridge 104. Again, cushioning may be added in select areas, either at the location or around the location where the ankle and heel are anticipated to be placed or surrounding the location where the ankle and heel are anticipated to be placed. Cushioning may be added with cutaways or surface definitions in the shape of a standard foot, ankle or heel corresponding to various positions anticipated for the foot 111.

FIG. 3B shows an end view of the device in FIG. 3A, with the foot 111 constrained against medial and/or lateral rotation by support device 100. The foot 111 is shown with the heel 112 resting on a lower heal depression of support surface 118. Also, sides of the ankle 113 are shown in contact with inner side surfaces 114, 116 of lateral ridges 102, 104. As illustrated, lateral ridges 102, 104 have a height such that least half of the foot (by length) is flanked on each side by inner side surfaces 114, 116. The height of lateral ridges 102, 104 above support surface 118 can be selected so that at least ⅓, at least ½, or at least ⅔ of the foot (by length) is flanked by inner side surfaces 114, 116. To accomplish this, lateral ridges 102, 104 can extend beyond support surface 118 by at least 3 inches, at least 3.5 inches, at least 4 inches, at least 4.5 inches, at least 5 inches, at least 5.5 inches, or at least 6 inches. On the other hand, lateral ridges 102, 104 can be shorter than a foot of standard length to provide ventilation to the foot, including unrestricted ventilation of the upper foot, permit freedom of movement of the toes, and facilitate ready access to the foot, such as to provide triage.

FIG. 3C shows an alternate perspective view of FIG. 3A. This view shows the foot 111 and a distal end of a lower limb 115 being supported by support surface 118. The distal end of lower leg 115 is also shown in contact with inner side surfaces 116, 114, FIGS. 3A, 3C both show only the foot and distal end of a patient's leg being supported in support device 100. The calf is not supported but is suspended by device 100 above a surface on which device 100 rests. This configuration permits the patient's knee (not shown) to remaining a more extended rather than bent position.

Those skilled in the art will appreciate that supporting heel 112, ankle 113, and lower limb 115 with the support surface 118 and constraining the foot 111 by inner side surfaces 114, 116 can minimize or prevent medial and/or lateral rotation of the patient's lower leg. With the foot, including ankle and heel, constrained by the device in this manner, it will be appreciated that medial and/or lateral rotational movements of the lower limb and foot can be minimized or prevented. For example, the following movements may be minimized or prevented:

Dorsiflexion: Bending the foot at the ankle toward the shin (bending the foot upward).
Plantar flexion: Bending the foot at the ankle toward the sole (bending the foot downward).
Eversion: Turning the foot so the sole faces laterally.
Inversion: Turning the foot so the sole faces medially.
Circumduction: Moving a part so that its end follows a circular path (moving the toes in a circular motion without significantly moving the ankle).

As discussed in the Summary, support device 100 can be modified to include a medial ridge positioned transversely between lateral ridges 102, 104 in order to limit plantar flexion of the foot during use. The medial ridge may, in cooperation with ridges 102, 104, also help limit or restrict eversion, inversion and/or circumduction of the foot.

In addition to minimizing or preventing movements of the foot, the support device may prevent medial and/or lateral rotational movements of the knee and overall leg that may otherwise be caused by medial and/or lateral rotation of the foot. The leg and knee may thus be protected against torsional effects and torque caused by medial and/or lateral rotation of the foot. Also, the foot and knee may be restrained from turning medially (inwardly) or laterally (outwardly), ensuring that the knee does not face a direction other than a direction that is parallel to the direction of the foot. Further, the device supports the foot and ankle such that free space is created proximally to the ankle in the region of the Achilles tendon and calf muscle. This free space allows the leg to drop into full extension at the knee without raising the heel away from the device.

In preventing medial and/or lateral rotation, a leg may be forced to remain in a generally fixed position such that ice may be applied to a region of the leg to reduce swelling or ease pain. In providing stabilizing support and isolation, the leg is better able to get proper rest and healing. If the foot or leg require to be moved, for example, to help adjust body position or remove the patient from the table, the device keeps the process simple because it is easy to install and remove.

Figure 4:
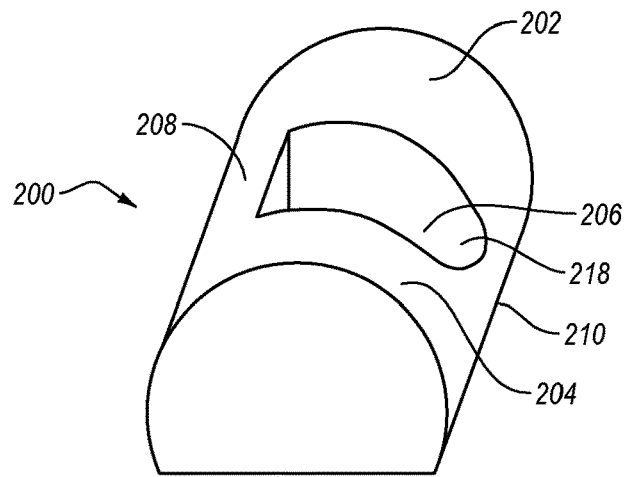
FIG. 4 is a perspective view of an embodiment of a device, which may include all of the features of the device in FIGS. 1-3C and further include a medial ridge between and transverse to the lateral ridges for additional foot immobilization, including restraint of foot rotation and limiting plantar flexion.
Figure 5:
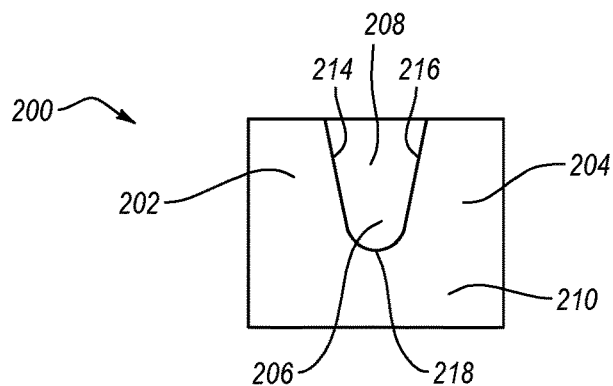
FIG. 5 is a front view of the device of FIG. 4 for lower limb elevation and foot immobilization, the device including a medial ridge between the lateral ridges.

FIG. 4 illustrates an embodiment of a support device 200 for lower limb elevation and stabilization that can be substantially similar to, or identical in every way compared to, support device 100 except that support device 200 further includes a medial ridge 208. As shown, and similar to support device 100, support device 200 includes a main body 210, lateral ridges 202, 204, a medial depression 206, a medial ridge 208, and a support surface 218. Medial ridge 208 extends along or near a distal end of medial depression 206 and can further support and restrain movement of the patient's ankle and foot. As shown, medial ridge 208 at the medial section may be continuous with lateral ridges 202, 204 so as to form a continuous medial ridge. Alternatives include, however, that medial ridge 208 not be continuous with lateral ridges 202, 204. Medial ridge 208 may have a similar width corresponding to widths of lateral ridges 202, 204. Alternatively, the width of medial ridge 208 may vary. Medial ridge 208 may have a similar height as lateral ridged 202, 204 as shown; however, the heights may differ. Turning to FIG. 5, support device 200 is shown with lateral ridges 202, 204 having angled inner side surfaces 214, 216 on opposing sides. Inner side surfaces 214, 216 are shown to taper downward and toward the center of the device 200. Alternatively, inner side surfaces 214, 216 can be rounded or vertical. With vertical inner side surfaces and a flat surface, a box-like shape may be present.

As shown, support surface 218 of medial depression 206 may be curved, with the curvature facing upward and joining angled inner side surfaces 214, 216. Alternatives include a flat support surface 218 that joins the angled inner side surfaces 214, 216. Support surface 218 as well as other surfaces of main body 210 may be smooth, pebbled, rough, textured, contoured, or have other features that improve and aid the user experience. For example, a textured surface may improve foot grip and thus further prevent movement. Support surface 218 can be contoured to accommodate the anatomy of the foot similar or identical to support surface 118 (e.g., by including cutouts, depression, inserts, elevational changes, curvatures, and the like as described above relative to support surface 118) in order to contact and support the heel and ankle. However, in preferred embodiments the calf is typically not supported by and does not contact the support device. In addition, the support device is configured to lift the foot to a height sufficiently above the surface upon which the patient lies so that the calf is suspended above the patient body support surface (e.g., bed). This helps keep the leg and knee in a straightened or extended configuration, which can be helpful when healing from many different types of knee surgery.

Figure 6A:
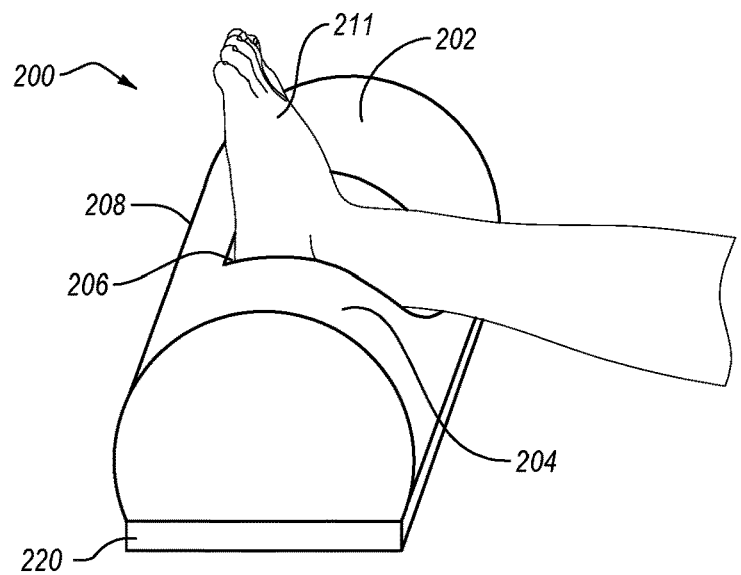
FIG. 6A is a perspective view of a foot inserted into the device of FIG. 4 for lower limb elevation and foot immobilization, with the lateral ridges limiting or preventing rotation and the medial ridge limiting plantar flexion.
Figure 6B:
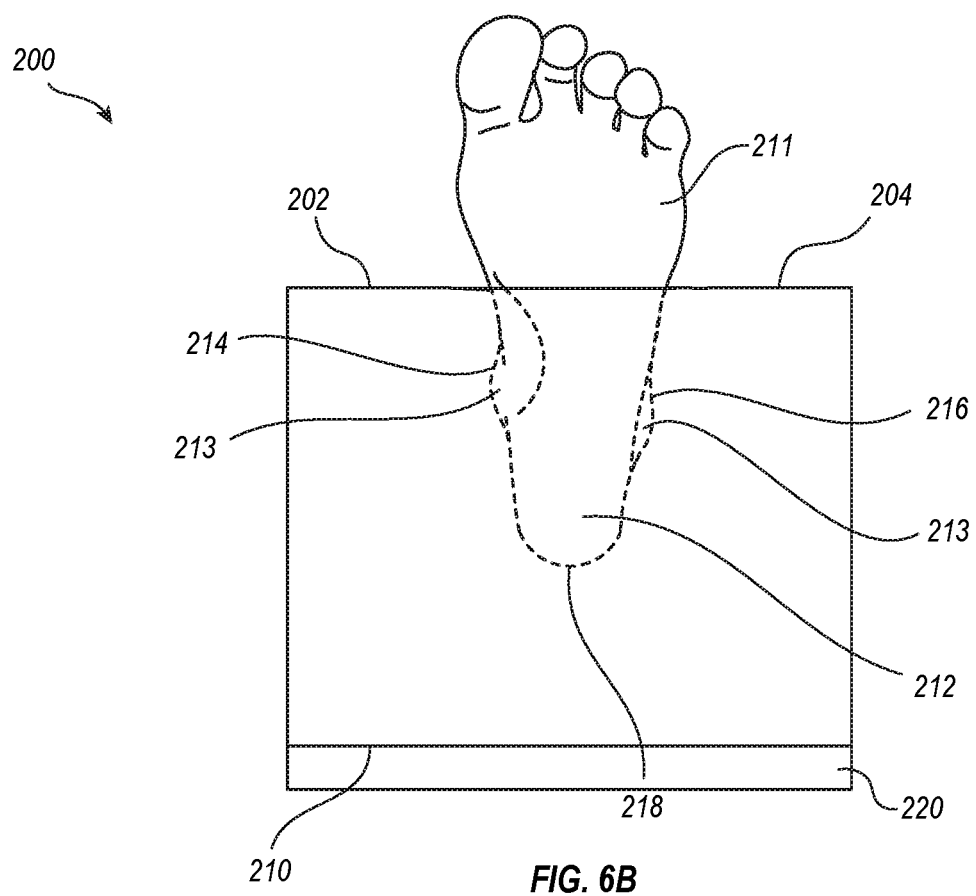
FIG. 6B is an end view of the device of FIG. 6A with a foot inserted into a device for lower limb elevation and foot immobilization, including restraint of foot rotation and limiting plantar flexion.

Turning to FIGS. 6A-6C, a foot 211 is shown inserted into device 200. With the addition of medial ridge 208, the foot 211 is prevented or limited from making movements, such as plantar flexion movements and other movements, such as eversion, inversion and/or circumduction. By further restraining the foot 211, the addition of medial ridge 208 may help further prevent medial and/or lateral rotation of the lower leg to better protect the knee joint. Medial ridge 208 may also aid the patient in inserting the foot 211 and removing the foot 211 from the device.

FIG. 6B shows an end view of the device of FIG. 6A looking through medial ridge 208, with the foot 211 constrained by device 200, including medial ridge 208. The foot 211 is shown with the heel 212 and lower surface of ankle 213 resting on support surface 218. Also, the sides of ankle 213 are shown in contact with inner side surfaces 214 and 216 of lateral ridges 202 and 204.

Many different materials can be used to manufacture the device. For example, the main body may comprise open cell polymer foam. Embodiments include that the polymer foam be coated with a flexible, fluid-impermeable polymer coating. Alternatives include that the device comprise radiolucent material. An advantage of open cell polymer foam is that it inherently resists slippage relative to a bed or other surface upon which is it placed.

With a given material, the main body may have a height and/or flexibility, coupled with sufficient firmness, so as to maintain a minimum elevation of the patient's ankle of at least 1 inch, at least 2 inches, at least 3 inches, or at least 4 inches, or at least 5 inches, from the upper surface of the supporting surface, during use (e.g., as illustrated in the drawings, FIG. 3B shows a foot elevated by about 3-4 inches and FIG. 6B shows a foot elevated by about 4-5 inches). Providing stabilized elevation may be helpful in keeping the leg immobilized at a desired height during a period of medical recovery. Embodiments include that the main body have a firmness with sufficient softness and yield to reduce pressure at and provide a comfortable support for high-pressure, soft-tissue areas.

Furthermore, support devices 100, 200 may include an auxiliary pad, such as flat auxiliary pad 220 illustrated in FIG. 6C, configured to be positioned directly beneath the main body to further elevate the patient's ankle during use. This permits adjustments to the height or elevation of support surfaces 118, 218 to accommodate specific needs of the patient. Auxiliary pad 220 can be made from the same open cell foam material as support devices 100, 200 and would advantageously prevent inadvertent slippage of the support device relative to the auxiliary pad and also relative to a bed or other surface upon which is it placed.

In using the device to elevate the patient's ankle during medical recovery, a stable platform, such as a bed or hospital bed, may be provided. The device may be placed on an upper surface of the stable platform. Proper positioning of the device may include putting the device underneath the ankle region of the patient, thereby elevating the ankle of the patient.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

The invention claimed is:

1. A device for supporting and elevating an ankle and heel of a patient's leg and restraining medial and lateral rotation of the patient's foot in order to protect the patient's knee following knee surgery, comprising:
    a main body having a generally flat bottom surface and lateral edges;
    two spaced-apart lateral ridges extending along or near the lateral edges of the main body and having inner side surfaces; and
    a medial depression between the lateral ridges that provides a support surface and a lower heel depression that accommodate natural contours of the ankle and heel and permit the heel to sink into the heel depression when the foot is positioned in the medial depression,
    wherein the lateral ridges are dimensioned to extend to a height above the support surface so that the inner side surfaces are adjacent to at least a majority of the patient's foot when placed in the medial depression to limit or prevent medial and lateral rotation of the foot,
    wherein the lateral ridges are spaced apart to provide an upper opening to the medial depression that is wider than the heel depression so as to facilitate downward placement of the patient's foot into the medial depression without manual manipulation and spreading apart of the lateral ridges,
    wherein the support surface is dimensioned so that it terminates at a location between the patient's ankle and calf so as to contact and support the patient's ankle but not the calf when the patient's foot is placed in the medial depression.

2. The device of claim 1, further comprising a medial ridge transverse to the lateral ridges, distal to the heel depression, and extending to a height above the support surface so as to limit plantar flexion of the foot.

3. The device of claim 1, wherein the device is devoid of walls that contact an anterior surface of a foot placed in the medial depression.

4. The device of claim 1, wherein the device is devoid of walls that limit dorsiflexion of a foot placed in the medial depression.

5. The device of claim 1, wherein at least a portion of a proximal upper surface of at least one lateral ridge has a downwardly angled slope declining from an upper extent of the lateral ridge towards a lower extent of the lateral ridge at a proximal end of the device.

6. The device of claim 1, wherein at least a portion of a distal upper surface of at least one lateral ridge has a downwardly angled slope declining from an upper extent of the lateral ridge towards a lower extent of the lateral ridge at a distal end of the device.

7. The device of claim 1, wherein the main body and lateral ridges comprise open cell polymer foam.

8. The device of claim 7, wherein the polymer foam is coated with a flexible, fluid-impermeable polymer coating.

9. The device of claim 1, wherein the device comprises radiolucent material.

10. The device of claim 1, wherein the main body has a firmness with sufficient softness and yield to reduce pressure at and provide a comfortable support for high-pressure, soft-tissue areas.

11. The device of claim 1, wherein the inner side surfaces of the lateral ridges define a greater width above the support surface to accommodate a talus bone of the ankle.

12. The device of claim 1, wherein the support surface is curved to approximately match the contour of a lower leg portion.

13. The device of claim 1, further comprising an auxiliary pad configured to be positioned directly beneath the main body to further elevate the patient's ankle during use.

14. A device for supporting and elevating an ankle and heel and restraining medial and lateral rotation of a patient's foot in order to protect the patient's knee following knee surgery, comprising:
    a main body having a bottom surface, lateral edges, and a width between the lateral edges greater than a length of the patient's foot;
    two spaced-apart lateral ridges extending along or near the lateral edges of the main body and having inner side surfaces;
    a medial depression between the lateral ridges that provides a support surface and heel supporting region configured to receive the patient's ankle and heel when the patient's foot is positioned in the medial depression; and
    a medial ridge transverse to the lateral ridges, distal to and extending above the heel supporting region of the medial depression to a height when the patient's foot is placed in the medial depression so as to limit plantar flexion of the foot,
    wherein the lateral ridges extend beyond the heel supporting region of the support surface by at least 4 inches to thereby confine and restrain a foot placed in the medial depression and limit or prevent medial and lateral rotation of the foot,
    wherein the support surface is dimensioned so that it contacts and supports the patient's ankle but not the calf when the patient's foot is placed in the medial depression to maintain knee extension, and
    wherein the lateral ridges extend to a height when the patient's foot is placed in the medial depression so as to provide unrestricted ventilation of at least an upper portion of the patient's foot.

15. The device of claim 14, wherein the device is devoid of walls that contact an anterior surface and a bottom surface of a foot placed in the medial depression.

16. A device for supporting and elevating an ankle and heel and restraining medial and lateral rotation of a patient's foot in order to protect the patient's knee following knee surgery, comprising:
   a main body having a generally flat bottom surface;
   first and second lateral edges extending between a proximal end and a distal end of the main body;
   two spaced-apart lateral ridges extending at least partially between the proximal end and the distal end and having inner side surfaces; and
   a medial depression between the lateral ridges that provides a support surface and distal heel region for receiving the ankle and heel of the patient's foot; and
   a medial ridge transverse to the lateral ridges,
   wherein the lateral ridges are dimensioned to extend above the distal heel region to a height above a majority of the patient's foot when the patient's foot is placed in the medial depression so as to limit or prevent medial and lateral rotation of the foot and allow unrestricted ventilation of at least an upper portion of the foot,
   wherein the support surface is dimensioned so that it terminates at a location between the patient's ankle and calf so as to contact and support the patient's ankle but not the calf when the patient's foot is placed in the medial depression,
   wherein the device is devoid of walls that contact an anterior surface of the patient's foot when placed in the medial depression, and
   wherein the medial ridge extends to a height above the distal heel region to limit plantar flexion of the foot and provide unrestricted ventilation of at least an upper portion of the patient's foot.

17. The device of claim 16, wherein the lateral ridges extend to a height of at least 4 inches above the support surface at the distal heel region.

18. The device of claim 16, wherein the lateral ridges are spaced apart so as to facilitate downward placement of the patient's foot into medial depression without manual manipulation and spreading apart of the lateral ridges.

19. The device of claim 16, wherein the medial ridge extends to a height no greater than the height of the lateral ridges.

20. The device of claim 1, wherein the lateral ridges extend to a height above the support surface of at least 5 inches.

* * * * *